(12) United States Patent
Hawker et al.

(10) Patent No.: US 10,478,147 B2
(45) Date of Patent: Nov. 19, 2019

(54) CALIBRATION APPARATUS AND METHOD FOR COMPUTED TOMOGRAPHY

(71) Applicant: NIKON METROLOGY NV, Leuven (BE)

(72) Inventors: Sam Hawker, Hertfordshire (GB); Gemma Fardell, Herfordshire (GB); Patrick Blankaert, Leuven (BE)

(73) Assignee: NIKON METROLOGY NV, Leuven (BE)

(*) Notice: Subject to any disclaimer, the term of this patent is extended or adjusted under 35 U.S.C. 154(b) by 382 days.

(21) Appl. No.: 15/100,192

(22) PCT Filed: Nov. 25, 2014

(86) PCT No.: PCT/EP2014/075568
§ 371 (c)(1),
(2) Date: May 27, 2016

(87) PCT Pub. No.: WO2015/078874
PCT Pub. Date: Jun. 4, 2015

(65) Prior Publication Data
US 2017/0020481 A1    Jan. 26, 2017

(30) Foreign Application Priority Data

Nov. 28, 2013 (GB) ................................. 1321003.4

(51) Int. Cl.
*A61B 6/00* (2006.01)
*G01N 23/046* (2018.01)
*A61B 6/03* (2006.01)

(52) U.S. Cl.
CPC .............. *A61B 6/583* (2013.01); *A61B 6/032* (2013.01); *A61B 6/584* (2013.01); *G01N 23/046* (2013.01)

(58) Field of Classification Search
CPC ......... A61B 6/583; A61B 6/032; A61B 6/584; G01N 23/046
See application file for complete search history.

(56) References Cited

U.S. PATENT DOCUMENTS

| 5,442,674 A | 8/1995 | Picard et al. |
|---|---|---|
| 7,147,373 B2 | 12/2006 | Cho et al. |
| 2005/0094771 A1 | 5/2005 | Basu et al. |
| 2005/0117708 A1* | 6/2005 | Cho .................. A61B 6/547 378/164 |

(Continued)

FOREIGN PATENT DOCUMENTS

| DE | 102008044437 A1 | 12/2009 |
|---|---|---|
| DE | 102010050949 A1 | 5/2012 |

(Continued)

OTHER PUBLICATIONS

Press, William H. et al., "Numerical Recipes in C" The Art of Scientific Computing, Second Edition, (1992).

(Continued)

*Primary Examiner* — Chih-Cheng Kao
(74) *Attorney, Agent, or Firm* — Birch, Stewart, Kolasch & Birch, LLP

(57) ABSTRACT

A calibration object is imaged in a radiographic system such as a CT system. The images are processed to calibrate the system, without prior measurement of the calibration object. Initial estimates are refined to improve accuracy.

28 Claims, 16 Drawing Sheets

(56) References Cited

U.S. PATENT DOCUMENTS

| | | | |
|---|---|---|---|
| 2007/0122020 A1* | 5/2007 | Claus | A61B 6/583 |
| | | | 382/131 |
| 2013/0230150 A1 | 9/2013 | Weiss | |
| 2014/0147028 A1* | 5/2014 | Zheng | A61B 6/5217 |
| | | | 382/131 |

FOREIGN PATENT DOCUMENTS

| | | |
|---|---|---|
| EP | 1760457 A2 | 3/2007 |
| JP | 4537090 B2 | 9/2010 |
| WO | WO 2005/015125 A1 | 2/2005 |

OTHER PUBLICATIONS

Richter-Gerbert, Jurgen, "Perspectives on Projective Geometry," A Guided Tour Through Real and Complex Geometry 2011.

Ford, Chetley, et al., "Estimation of CT cone-beam geometry using a novel method insensitive to phantom fabrication inaccuracy: Implications for isocenter localization accuracy", Med. Phys. 38, 2829-2840, (2011).

Guang Jiang, et al. "Single Axis Geometry by Fitting Conics", ECCV, LNCS 2350, pp. 537-550 (2002).

Gurdjos, Pierre et al., "Euclidean Structure from N 2: 2 Parallel Circles: Theory and Algorithms", ECCV 2006, Part I, LNCS 3951, pp. 238-252 (2006).

Jiang, Guang, et al., "Recovering the Geometry of Single Axis Motions by Conic Fitting", CVPR 2001, ISBN 0-7695-1272-0/01 (2001).

Mendonca, Paulo et al., "Epipolar Geometry from Profiles under Circular Motion", IEEE Transactions on Pattern Analysis and Machine Intelligence, vol. 23, No. 6 (Jun. 2001).

Rosin, Paul L., "A note on the least squares fitting of ellipses", received Feb. 4, 1992, Pattern Recognition Letters 14 (Oct. 1993) pp. 799-808.

Wong, Kwan-Yee et al., "Camera Calibration from Surfaces of Revolution", IEEE Transactions on Pattern Analysis and Machine Intelligence, vol. 25, No. 2, (Feb. 2003).

Wu, Yihong, et. al., "Camera Calibration from the Quasi-affine Invariance of Two Parallel Circles", ECCV, LNCS 3021, pp. 190-202 (2004).

* cited by examiner

CALIBRATION APPARATUS AND METHOD FOR COMPUTED TOMOGRAPHY

The invention relates to a calibration method for an X-ray computed tomography (CT) system using a dedicated (but not necessarily calibrated) calibration object (phantom).

X-ray imaging is a known technique for analysing a sample, for example, for measurement or inspection. X-rays emitted by the source are attenuated by the sample and detected by the detector. The degree of attenuation of X-rays passing through the sample, and therefore the intensity of the X-rays detected by the detector, depends on characteristics of the sample. For example, parts of the sample that are strongly X-ray attenuating typically appear as darker areas on the detector image.

As a result, information about the structure, including the internal structure, of a sample can be obtained.

In two-dimensional X-ray imaging, normally only a single image of a sample is taken, which provides only limited depth information about the structure of the sample.

In computed tomography (CT) X-ray imaging, a plurality of two-dimensional projected images of a sample are acquired, for example, by rotating the sample relative to the source and detector. Typically, the sample is placed on a mount, such as a turntable, and the mount is rotated about a rotation axis, in successive angle increments. The resulting two-dimensional images are processed to reconstruct a three-dimensional representation of the sample.

The reconstruction uses parameters of the CT system. Thus, in order to have an accurate reconstruction of the sample, it is important for the parameters of the CT system to be accurate. For example, CT systems are used for measurement of internal and external dimensions of samples, such as aircraft components, where accuracy is needed to the highest degree possible. Similarly, the parameters of the system need to be accurate to a high degree.

In other words, the greater the accuracy the parameters of the CT system, the greater the accuracy of the reconstruction.

It is known to determine parameters of a CT system by calibration (see, for example, [1] to [5], [12]. More specifically, a sample having known characteristics (typically described as a calibration object, artefact or phantom) is imaged by the system. The resulting images are analysed, using known characteristics of the sample, to determine parameters of the system, for use in subsequent imaging of other objects.

The calibration object has a plurality of markers arranged in a known configuration, in a supporting material. Typically, the markers are strongly X-ray attenuating, and the supporting material is weakly X-ray attenuating, so that the markers stand out on the X-ray images. The calibration object is imaged in the CT system as outlined above. The calibration object is also measured using another metrology method, such as using an optical scanner or touch probe attached to a coordinate measuring machine arm (CMM arm). For example, measurements, for example, distances between markers, as obtained by the CT system and by the alternative metrology method can be compared, and used to calibrate the CT system.

Examples of known calibration objects, and methods for calibrating CT systems using calibration objects, are described in references [1] to [6].

The calibration methods in [1], [2], [3], [4] and [5] require accurate information, prior to calibration, especially about the 3D relative positions of the markers, and any errors have a direct influence on the accuracy of the calibration method. In [6] efforts are made to reduce but not eliminate the influence.

Reference [12] relates to a method of determining magnification in a system such as a CT system, using a known distance between different positions of a workpiece. The results of are limited accuracy.

Reference [17] relates to a method of determining a rotation axis in a tomosynthesis device by adding a plurality of projection images, and using the fact that the added projection image is symmetrical with respect to the rotation axis.

The method of reference [17] does not use a dedicated phantom containing markers, and is only able to determine 2 geometry parameters.

The object of the invention is to address the problems of the prior art.

Aspects of the invention are set out in the claims.

According to one aspect, the invention provides a method of calibrating a radiographic system comprising a source and/or a detector, the method comprising providing a calibration object rotating the calibration object relative to the source and/or detector, around an axis of rotation, acquiring a plurality of radiographic images of the calibration object, assigning a nominal value representing the distance between the source and the axis of rotation, and determining geometrical parameters of the system using said radiographic images and said nominal distance.

According to another aspect, the invention provides a method of calibrating a radiographic system comprising a source and/or a detector (for X-rays), the method comprising providing a calibration object, rotating the calibration object relative to the source and/or detector, acquiring a plurality of radiographic images of the calibration object, and determining geometrical parameters of the system using said radiographic images, without requiring or using prior information regarding the calibration object, that is, information obtained by means other than the system being calibrated, at least in the initial estimation.

In other words, geometrical parameters of the system are derived from the images of markers, without use of accurate measurements of the locations of markers in the calibration object itself. To provide information regarding scale, an additional 403 measurement to introduce a length standard (corresponding to the nominal distance above) may be required.

According to another aspect, the invention provides a method of calibrating a radiographic system comprising a source and/or a detector, the method comprising providing a calibration object, rotating the calibration object relative to the source and/or detector, acquiring a plurality of radiographic images of the calibration object, wherein the calibration object comprises a plurality of markers, the method comprising identifying a plurality of markers in a plurality of images, deriving an elliptical path for each of a plurality of markers using said images, preferably by fitting an ellipse to the imaged trajectory of each of the markers, and using said elliptical paths to determine geometrical parameters of the system.

It is the fitting of ellipses to the 2-dimensional imaged trajectories of at least two markers that enables the geometrical parameters of the system to be determined, as described below.

Preferably, the calibration object is rotated around the rotation axis. The calibration object may be mounted on a mount, for example, a rotatable mount. The mount may also allow the calibration object to be translated, for example, in 3 perpendicular directions. Alternatively, the source and/or detector may be rotated around the calibration object, and may also be translated relative to the calibration object.

The plurality of radiographic images are different images corresponding to different projection directions of the X-rays. In other words, the images are taken at different relative degrees of rotation.

Embodiments of the invention derive an initial estimate of geometrical parameters of the system, which are further refined. This increases the accuracy.

The invention also provides a suitable calibration object.

A dedicated phantom is constructed by arranging spherical markers of a strongly X-ray attenuating material (e.g. tungsten carbide precision ball bearings) in low-density foam of a weakly X-ray attenuating material. Radiographic images of the phantom are taken in a number of positions and orientations. The 2D image coordinates are determined for each marker in each radiograph. A system of non-linear equations is set up to express these 2D image coordinates in terms of the 3D relative positions of the markers as well as the geometry parameters of the CT system. A least-squares solution is found using a non-linear iterative solver. Where accurate information about the 3D relative positions of the markers or about the geometry parameters of the CT system or about the positions and/or orientations of the phantom is available it may be used to improve the robustness of the solution.

In this invention accurate prior information about the 3D relative positions of the markers is not required in order to calibrate the system. As a result accuracy can be improved, because errors possibly arising from measurement of the markers are not introduced into the calibration. The calibration is self-consistent, and depends only on the system and phantom, in the conditions at the time. The calibration can also be made faster and more efficient, and simpler and more cost-effective, because additional measuring devices are not required. Calibration can be done on-site, without the need for additional measuring devices or information. For example, the owner of the system can calibrate the system without needing to rely on the manufacturer. This method is able to determine 6 geometry parameters (or 7 geometry parameters after the introduction of a length standard).

The phantom fabrication precision need only be sufficient to ensure markers do not overlap in the radiographic images. The phantom need not be measured (e.g. with a contact or optical CMM) and need not be dimensionally stable over prolonged periods. This allows the phantom to be low cost and also allows it to be better optimised for its radiographic properties.

The use of low density plastic or ceramic foams (and also the absence of adhesives) in a phantom for X-ray CT calibration allows the markers to be imaged more clearly than in the prior art.

If the markers have to be measured using a contact CMM, as in the prior art, then the supporting structure must be much more open to allow access to the CMM probe. Additionally the supporting structure must not deflect under the force of the CMM probe. Furthermore the measurements must remain valid over prolonged periods (i.e. between re-measurements using the contact CMM).

All of these factors mean that generally a foam does not provide enough structural stability and so is not suitable in prior art techniques.

Similarly, according to the invention, adhesives, for example, for fixing the markers, are not required. It is important that the markers do not move during the calibration process. They can be fixed in place as a result of being forced into the foam. Adhesive has a similar attenuation to solid plastics (that is, higher than low density foam), and so avoiding adhesive can result in higher contrast images. In an embodiment of the invention, the calibration object can be made by embedding markers, such as ball bearings, in a solid plastic. Compared with a foam supporting structure, there would be a slightly lower contrast, but the images would still be quite clear because the supporting material would be very uniform.

The method of refining the 2D image coordinates of the markers is more accurate than the prior art. As a result of the method, and refinements, the image co-ordinates can be located to sub-pixel level, up to of the order of $\frac{1}{200}^{th}$ of a pixel. The efficacy of this aspect of the method depends on the markers being imaged very clearly.

The invention also provides an apparatus, for example, CT system, and computer program, or computer-readable storage medium storing a computer program, for executing the method.

The radiographic system is preferably an X-ray system, more specifically, an X-ray CT system.

Embodiments of the invention will be described with reference to the accompanying drawings of which:

Figure 16:
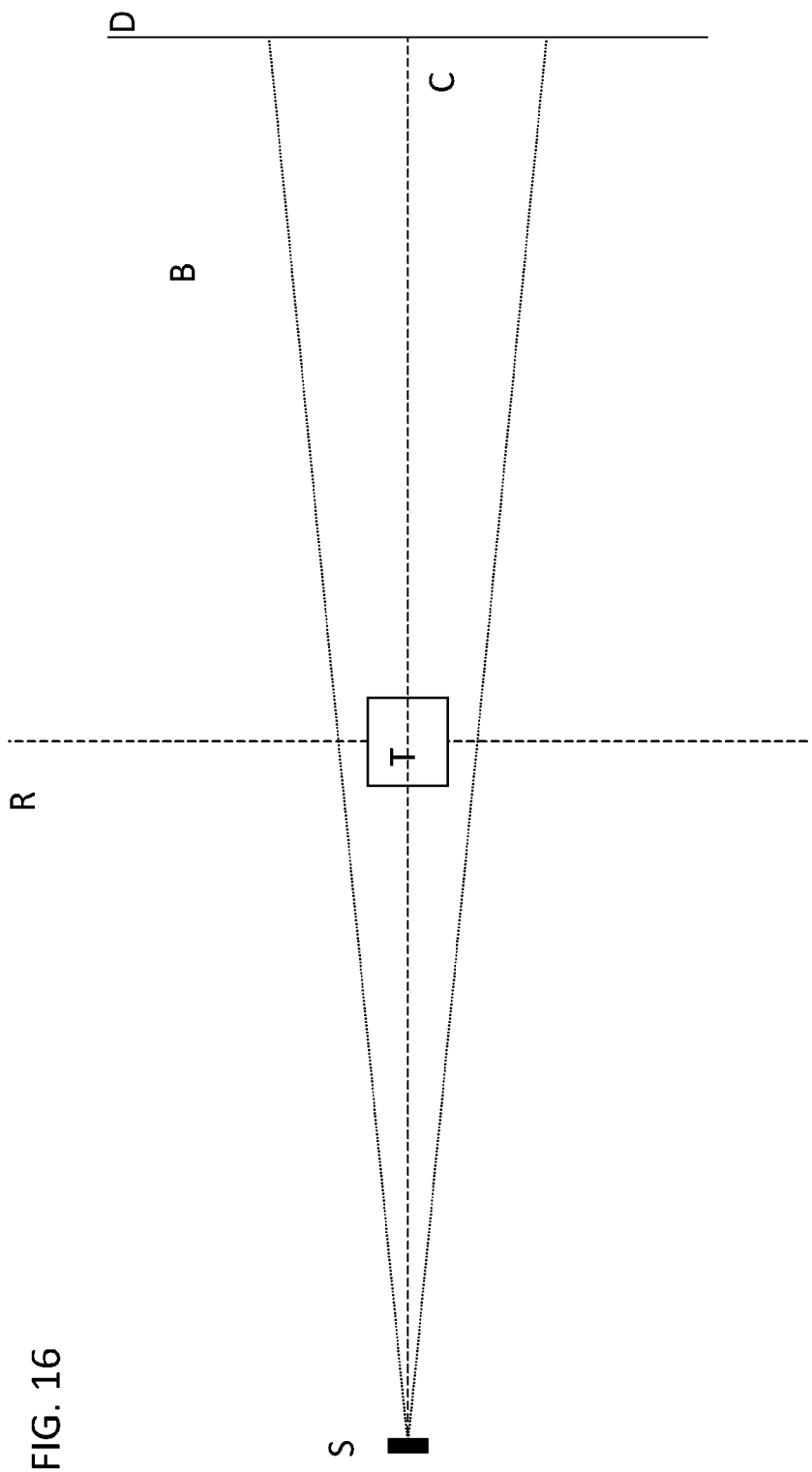
FIG. 16 is a general representation of a CT system.

A diagram illustrating the general principles of radiographic X-ray imaging is shown in FIG. 16. A source S emits X-rays in a beam B having a centreline C towards a detector D. A target object T is arranged between the source S and detector D, on an axis of rotation R.

In CT imaging, the target object T is rotated around axis R incrementally. After each increment of rotation, a 2-dimensional projected image is obtained by detector D. The plurality of images (radiographic projections) are processed to construct a 3-dimensional volume representation (volume map) of the target object.

Techniques for constructing the volume map from the 2-dimensional images are known to the person skilled in the art.

In order to create the volume map, certain geometrical parameters of the CT system need to be known, such as the location of the source S, the location of the detector D, and the axis of rotation R. Identifying these parameters accurately is performed by calibration.

Figure 1:
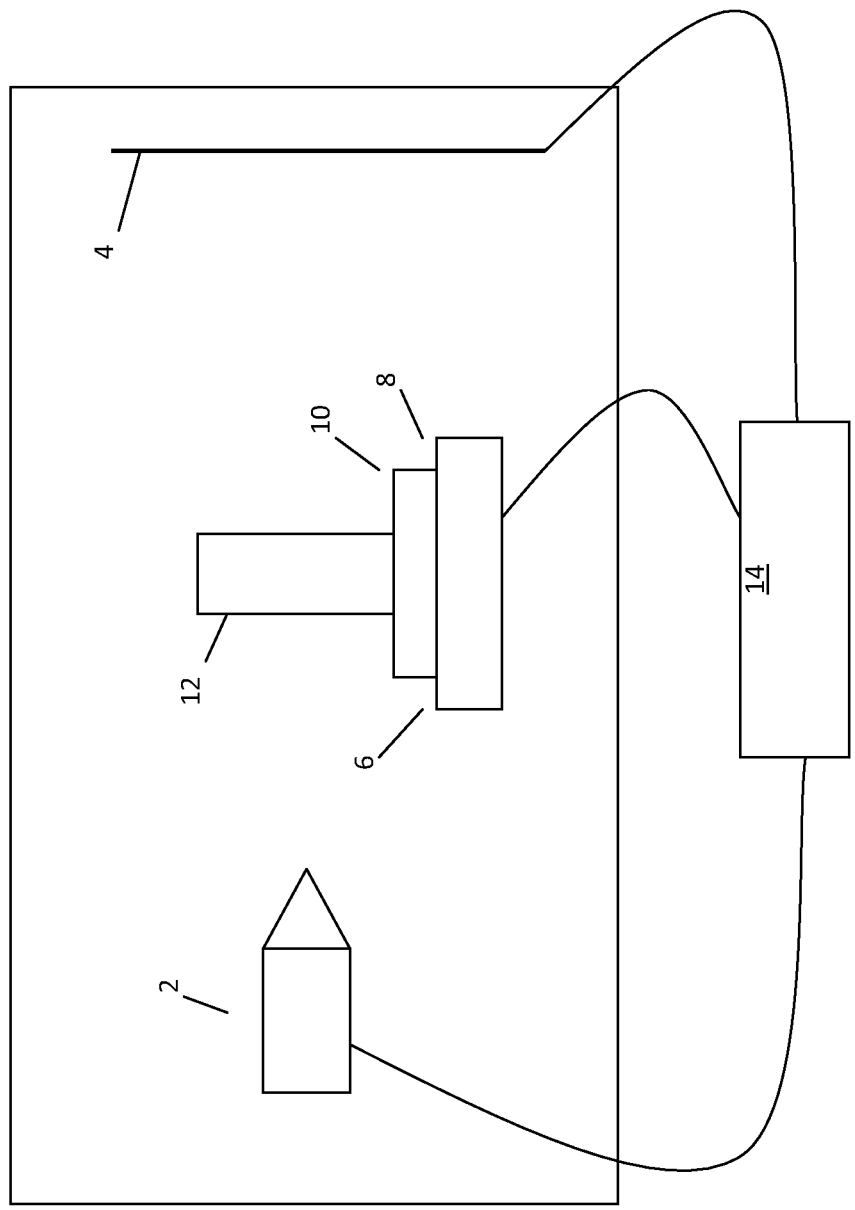
FIG. 1 is block diagram of CT system.

FIG. 1 shows an embodiment of a CT imaging system. The system has a source 2, which emits X-rays in a conical beam (not shown), and a detector 4 for detecting X-rays emitted from the source 2.

A sample mount 6 is provided between the source 2 and the detector 4. The sample mount 6 includes a platform 8, and a turntable 10 on the platform 8. A sample 12 is mounted on the platform 8. The platform 8 can be translated along the beam centreline (x axis), and in perpendicular axes in a plane perpendicular to the beam centreline (y and z axes), using a manipulator (not shown). The turntable 10 rotates about a rotation axis (not shown I FIG. 1, but discussed in more detail below).

A controller in the form of a control computer 14 controls the source, detector and sample mount. The controller 14 also obtains image data from the detector 4 and reconstructs the volume map. The controller 14 also performs calibration, to determine the geometrical parameters of the CT system, as described in more detail below. Alternatively, the image data can be transferred from the CT system for subsequent processing elsewhere.

To perform calibration, a dedicated calibration object, known as a phantom or artefact, is used as the target sample.

Figure 2:
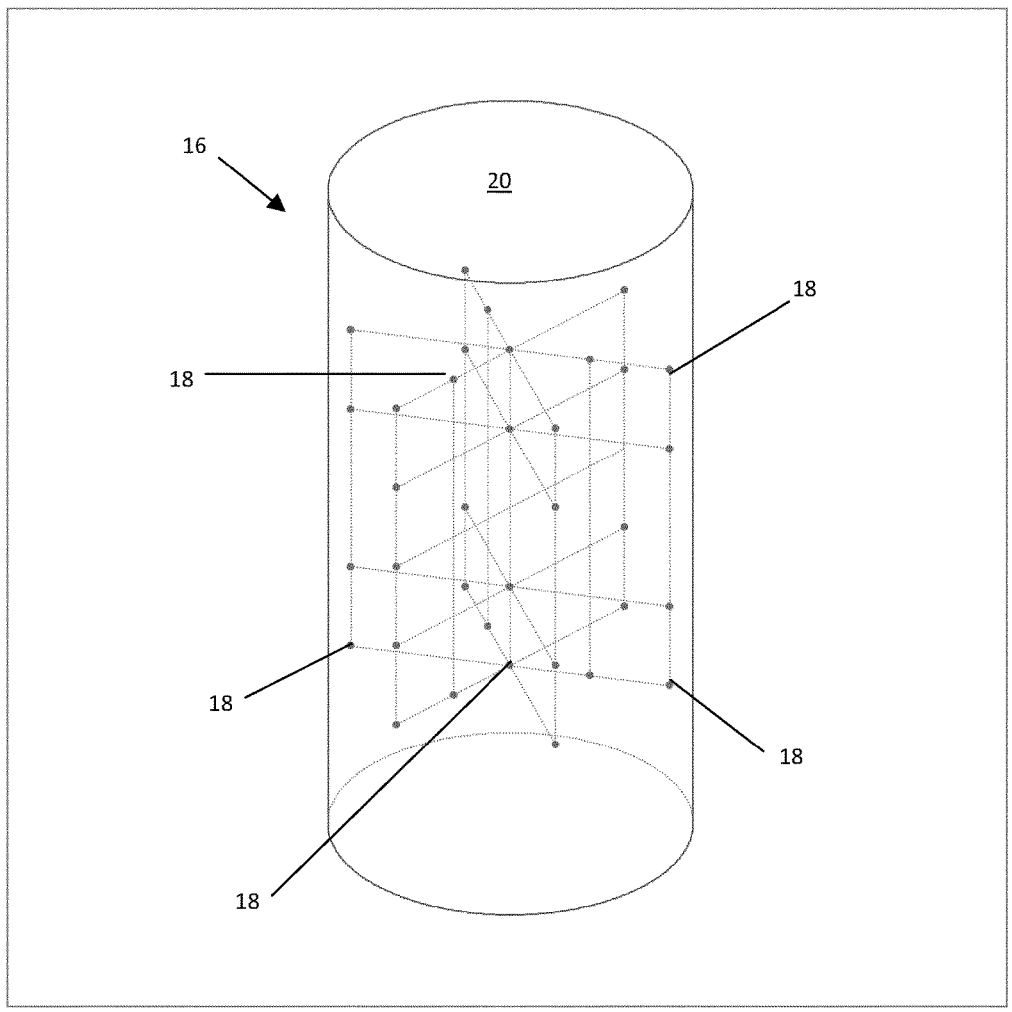
FIG. 2 is a diagram of a phantom according to an embodiment of the invention.

FIG. 2 shows a phantom 16 according to an embodiment of the invention.

The phantom is constructed by arranging a plurality of markers 18 in a supporting material 20. The markers 18 are strongly X-ray attenuating (radiodense, or relatively opaque to X-rays) in order to provide high contrast radiographic images in which the markers can be easily identified. The markers are highly spherical so that the 2D image coordinates of the centre of each marker can be determined with very high accuracy. In the embodiment, the markers 18 are formed of tungsten carbide precision ball bearings. The markers 18 are retained in the supporting material 20 without the use of adhesives. The markers 18 are arranged with respect to each other so as to minimise overlap in the intended radiographic images. Preferably, the markers 18 are arranged so as to never overlap in the intended radiographic images. An example of a suitable arrangement is shown in FIG. 2, but other arrangements are possible, such as disclosed, for example, in [3]. Suitable arrangements can be designed, for example, by modelling, or by inspection. Preferably, at least one marker is close to the central axis of the phantom and at least one other marker is spaced further away from the central axis, as in FIG. 2. In other words, the markers include markers radially spaced, preferably at least one marker close to the central axis and at least one marker close to the outer circumference of the phantom. The supporting material 20 is weakly attenuating (radiolucent, or relatively translucent to X-ray) so that the outline of each marker is imaged as clearly as possible. The supporting material 20 is preferably a low-density foam composed primarily of materials with low atomic number. Preferably the supporting material 20 is rigid, uniform and has a low thermal expansion coefficient. Carbon or silicon carbide foams are therefore considered ideal. Plastic foams such as extruded polystyrene foam are less favourable but may produce acceptable results. Other suitable materials include solid plastics and ceramics.

The phantom 16 is placed in the X-ray CT system of FIG. 1 and radiographic images are taken in a number of positions and orientations. Preferably the acquisition includes one complete rotation (in small angular increments) with the rotation axis imaged in the region of the centre of the detector. This central scan is important since this is the position where CT acquisition will normally take place.

Figure 3:
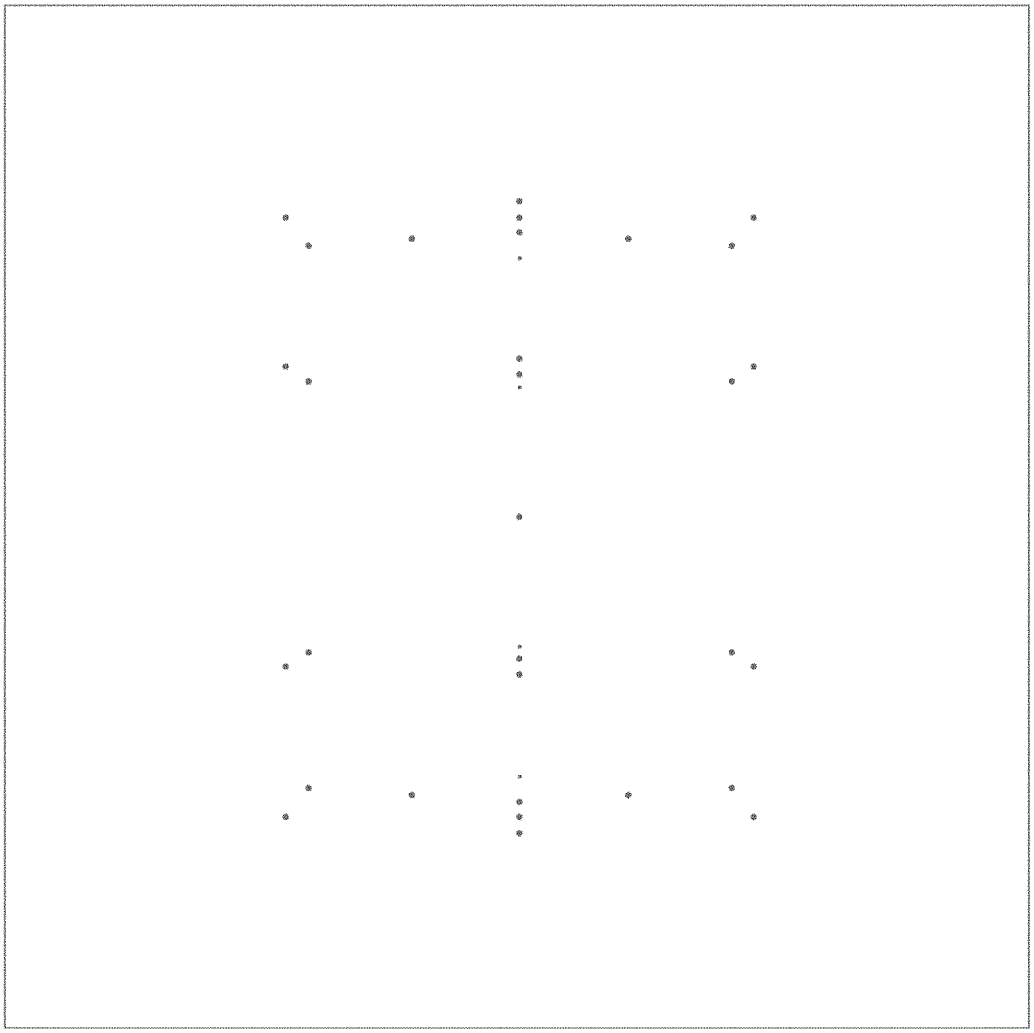
FIG. 3 is a first radiographic image of the phantom of FIG. 2.

FIG. 3 shows an example of a radiographic image of the phantom 16 of FIG. 2 from a central scan.

Preferably the acquisition also includes one complete rotation with the rotation axis imaged significantly toward the left- or right-hand side of the detector (but where the entire phantom 16 still remains in view). This offset scan is important since data from the central scan alone does not fully decouple all of the required geometry parameters of the CT system.

Preferably, the misalignment of the rotation axis relative to the detector is zero or close to zero in the central scan, and is significantly greater than zero, and preferably as large as possible, in the offset scan.

More specifically, for misalignment angles "skew" (in the plane of the detector, with respect to rotation axis "z" and perpendicular axis "x"), "slant" (around rotation axis z), and "tilt" (around axis x), preferably in the central scan slant is nominally equal to zero, and in the offset scan slant is non-zero.

Errors (i.e. differences between the values used during reconstruction and the true values) in tilt, slant and skew (as well as errors in the other geometry parameters) can have various effects, such as blurring, in part or all of reconstructions, or incorrect scaling.

Prior art techniques for addressing such problems have limitations. For example, in one technique, it is assumed that misalignment (in particular, slant or tilt) is close to zero, which reduces accuracy (especially for tilt), and causes distortion. In another technique, a large slant is introduced to enable tilt to be determined, but this then requires subsequent CT acquisition to be performed at the same slant, which is additional complexity and makes reconstruction more sensitive to errors.

In the present technique, a central scan with slant close to zero means small errors in the geometry parameters have the smallest effect. Slant can be introduced by translating the rotation axis sideways, without changing the relationship between the X-ray source and the detector. By having a non-zero slant in the offset scan, ambiguities in the calculations can be resolved.

A CT acquisition is usually done with slant, skew and tilt close to zero in order to make the reconstruction of an object as insensitive as possible to errors in slant, skew and tilt. Thus, likewise, calibration preferably involves a central scan in similar conditions. However, without additional information there is complete ambiguity in tilt in (where slant is equal to 0) or very poor accuracy in tilt (where slant almost equal to 0). These ambiguities can be resolved by the offset scan.

In order to link the information from the central and offset scans, invariants between the two scans are required. In the present embodiments, this is, for example, the positions of the markers in the phantom, and the relationship between the X-ray source and the detector (specifically the position of the principal point and the source to detector distance).

Figure 4:
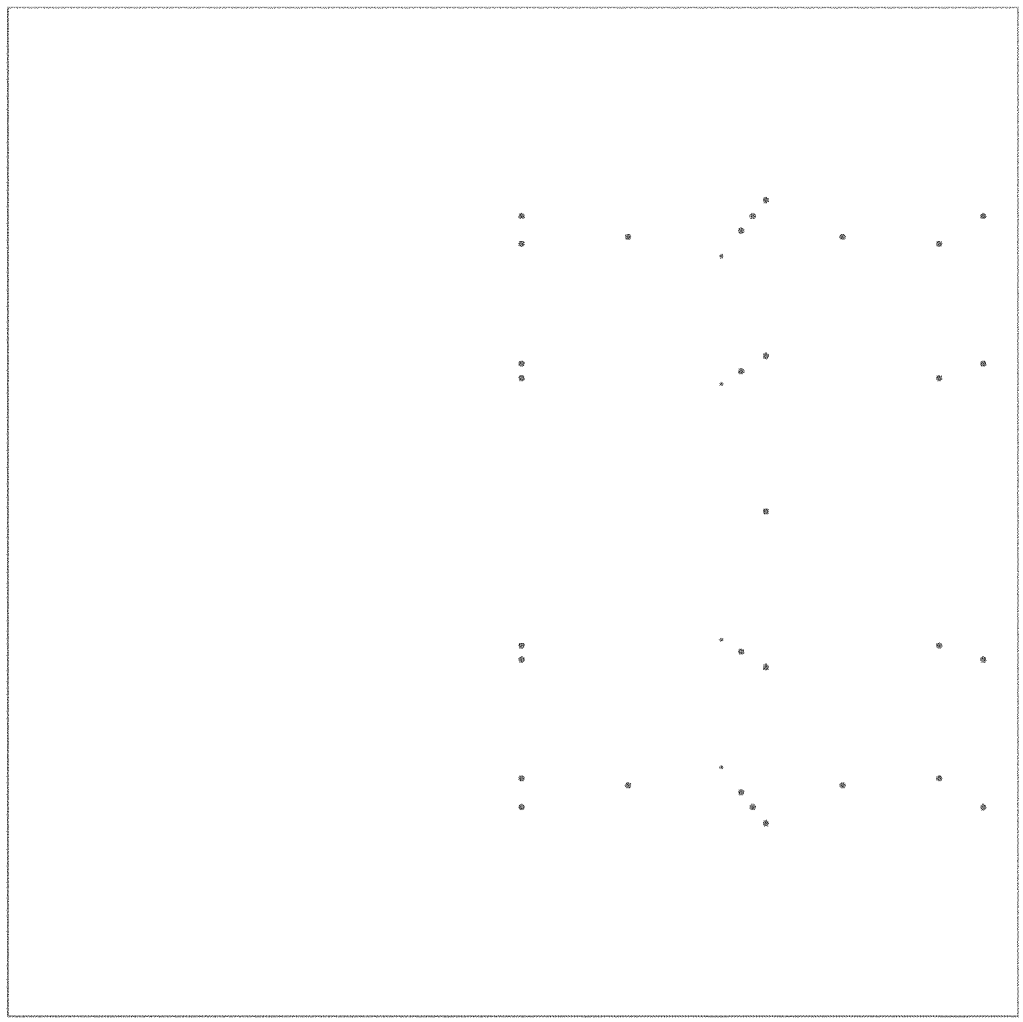
FIG. 4 is a second radiographic image of the phantom of FIG. 2.

FIG. 4 shows an example of a radiographic image of the phantom 16 of FIG. 2 from an offset scan.

Preferably the acquisition also includes images taken at different magnifications (with the phantom 16 moved towards and/or away from the source) and in different vertical positions. This is important to provide information about the directions of the manipulator axes relative to the detector pixel row and column directions. Preferably the entire phantom 16 is in view in each captured image, but this is not essential, provided there are at least 2 markers 18 which remain in view during a rotation.

Figure 5:
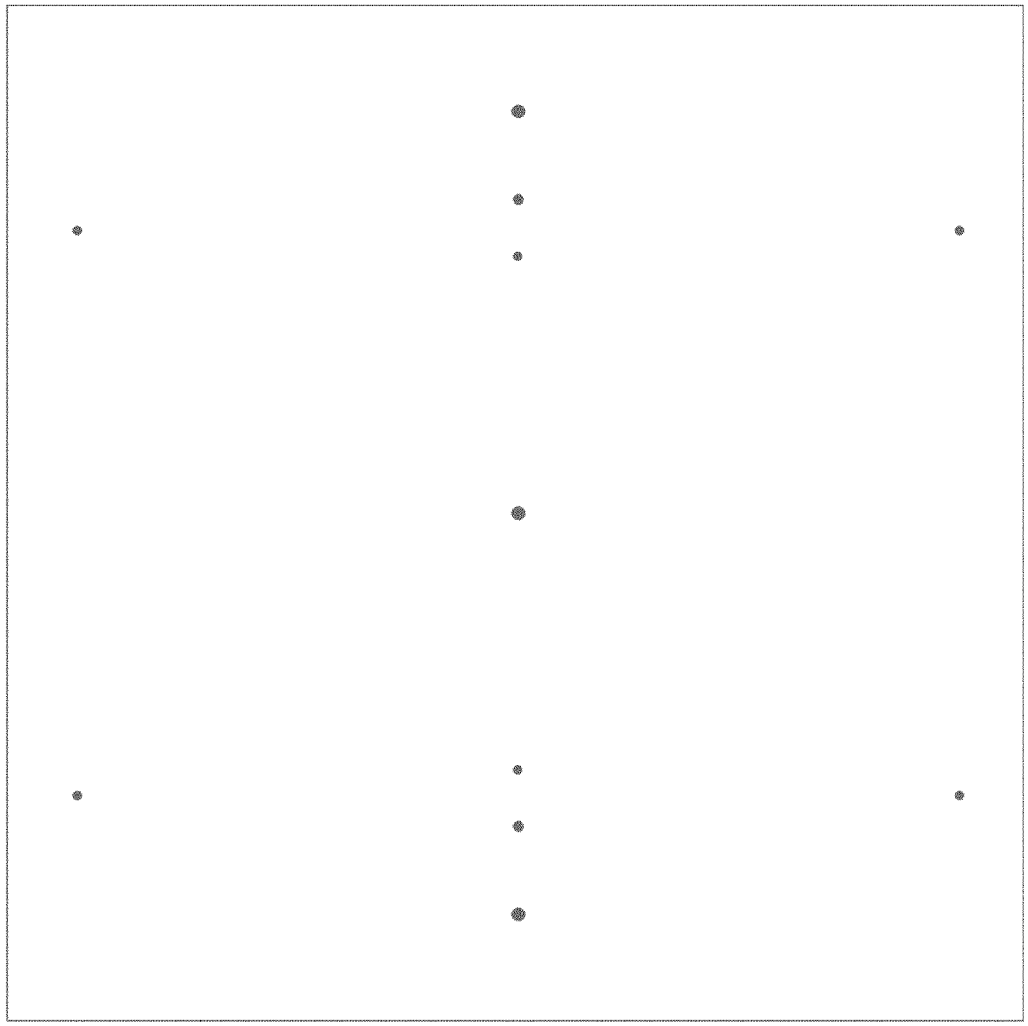
FIG. 5 is a third radiographic image of the phantom of FIG. 2.

FIG. 5 shows an example of a radiographic image of the phantom 16 from a scan at higher magnification.

The complete acquisition might take some considerable time (perhaps 4 hours or more) and there is therefore some possibility that changes might occur in the geometry parameters of the system or the 3D relative positions of the markers 18 (e.g. as a result of thermal changes). For this reason it might be beneficial to repeat the acquisition of a subset of the radiographic images within a reduced time window (at the beginning, at the end or in the middle of the acquisition). This fast scan allows long-term trends in the slow scan to be identified and compensated for in the subsequent analysis. This can be achieved by comparing the trajectories of the markers in the fast and slow scans.

The radiographic images are then analysed to determine the 2D image coordinates of the markers.

Figure 6:
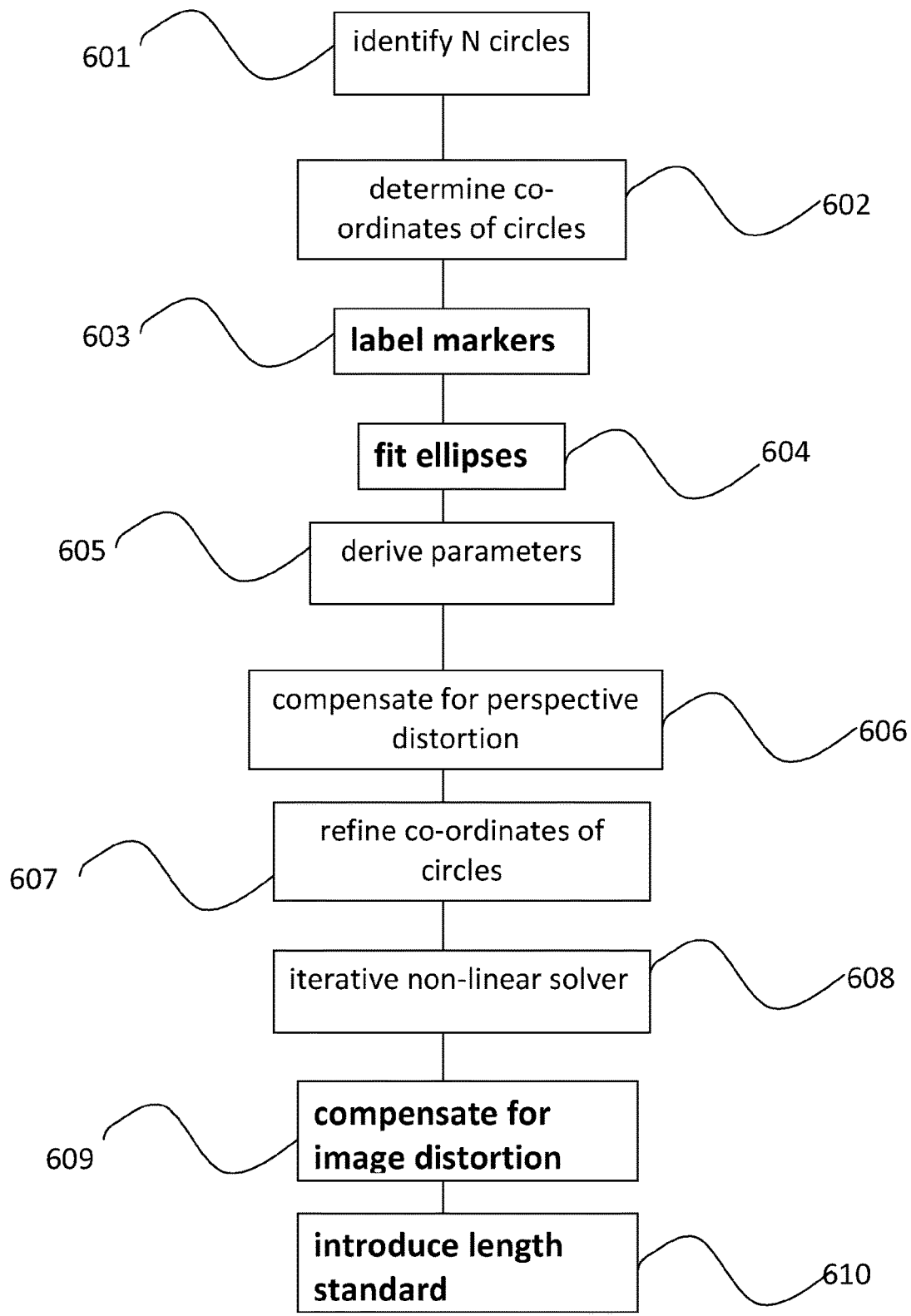
FIG. 6 is a flow diagram illustrating steps of the method of an embodiment of the invention.

With reference to FIG. 6, steps of the calibration method according to an embodiment of the invention are set out below. The method involves deriving a first approximation of the geometrical parameters of the CT system, followed by performing various refinements, to progressively improve accuracy.

In general terms, the method according to an embodiment involves defining the unknowns (unknown parameters), determining redundant degrees of freedom, measuring the phantom 16 in an offset position, extracting marker centre coordinates, calculating an initial geometry estimate, performing an iterative non-linear least squares estimate, and analysis of residual errors. This is described in more detail below.

In the first stage of the analysis according to an embodiment a circle-detection routine, more specifically, a Canny edge-detection and Hough circle-detection routine, is used to identify circular shapes in the image with approximately the correct diameter (step 601). This is to identify the parts of the image that may correspond to the images of the markers 18. The circle-detection routine identifies a plurality of circular shapes in the image, each having an associated "score", with a strong response or score indicating a greater likelihood that the corresponding shapes are circular. If the phantom 16 contains a total of N markers then typically the strongest N responses to the circle-detection routine are selected. Having identified the markers in a single image the approximate coordinates of the markers 18 in adjacent images in the sequence can be predicted. The accuracy of the prediction can be improved once the markers have been identified in two or more images.

In the next stage of the analysis the 2D image coordinates of the markers (the co-ordinates of the projected image of the markers) are refined (step 602). This is done by extracting radial intensity profiles at a number of different angles. Bi-linear interpolation is used although other interpolation schemes might also be suitable. For each radial intensity profile the point of maximum gradient is determined and the coordinates of this point are converted back to Cartesian coordinates. A circle is then fitted to these points using a least-squares method. The points of maximum gradient as well as the diameter and centre of the fitted circle are all stored for later use.

The markers are given numeric identifiers based on (approximate) prior information about the 3D relative positions of the markers 18 (step 603). This can be done, for example, simply by inspection, and does not require measurement. To avoid ambiguity the arrangement of the markers within the phantom is preferably asymmetric.

The 2D image coordinates from the offset scan are then analysed to determine an initial estimate of the geometry parameters of the CT system and of the position and orientation of the rotation axis, as discussed in more detail below. In general terms, this is done by recognising that during the rotation of the calibration object each marker traces an elliptical path on the detector (in other words, the path of the image of each marker in the plurality of images is elliptical). Ellipses are fitted to the 2D image coordinates of two or more of the markers (step 604). From the equations of these ellipses it is possible to obtain (step 605) the equation of the line on the detector 4 that is the image of the central slice (i.e. the image of the plane that is perpendicular to the rotation axis and contains the X-ray source point). It is also possible to obtain the coordinates of the principal point (i.e. the image of the line that is perpendicular to the detector and contains the X-ray source point) as well as the perpendicular distance from the X-ray source point to the detector, and therefore the location of the source S. Finally it is possible to obtain the equation of the line on the detector that is the image of the rotation axis.

A method of determining the initial estimate according to the embodiment is described in more detail below.

Figure 7:
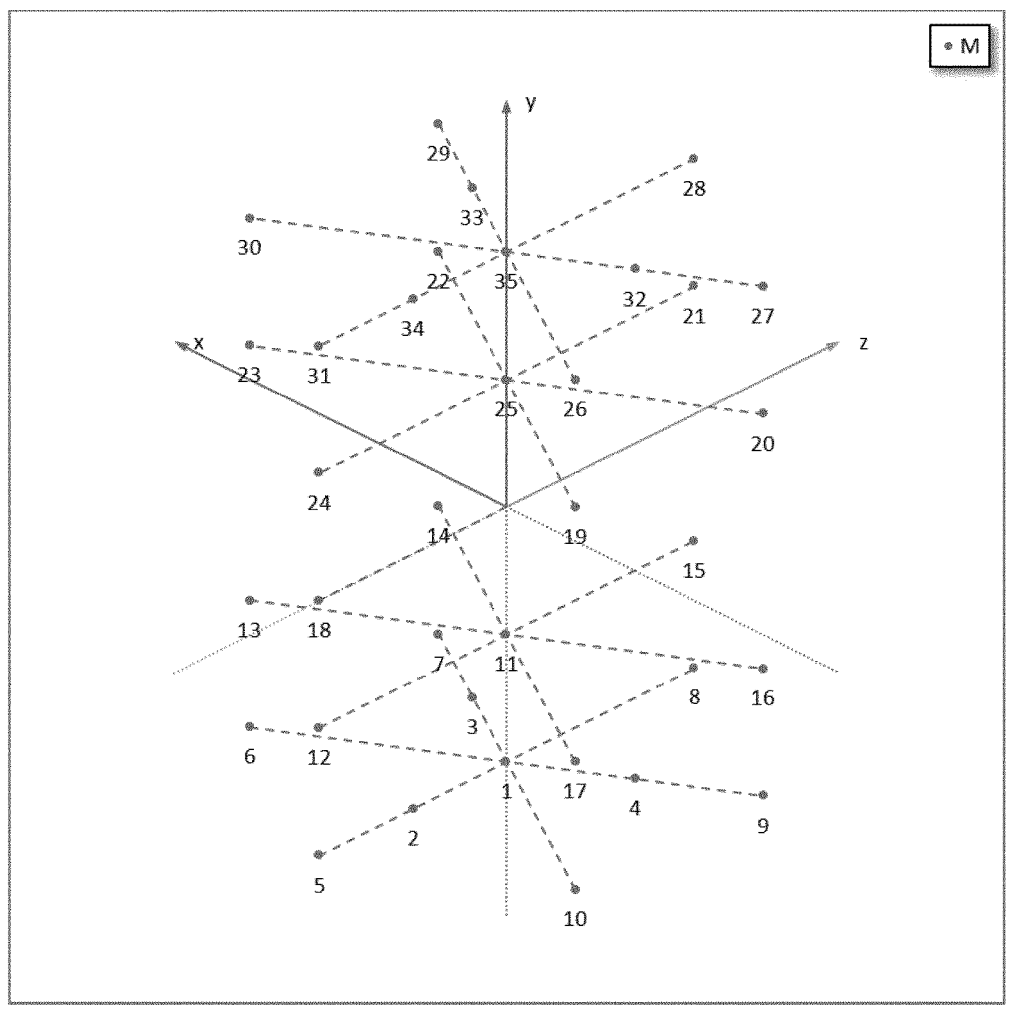
FIG. 7 is a representation of markers in a phantom.

FIG. 7 is a representation of the phantom 16, with the individual markers numbered, in co-ordinate system (x, y, z).

Figure 8:
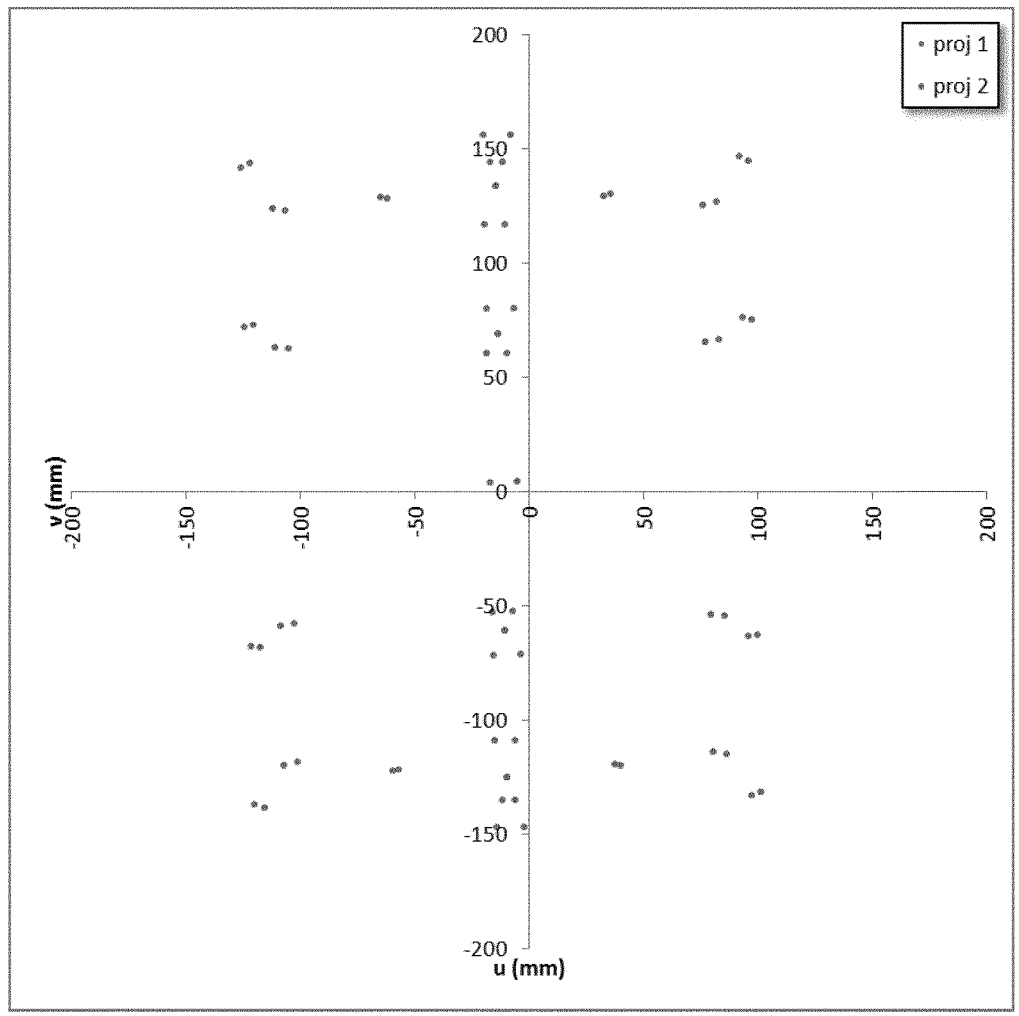
FIG. 8 shows a combination of two radiographic images of a phantom in a central scan.

FIG. 8 shows examples of two radiographic images (projections) in the central scan, in co-ordinate system (u, v), in the plane of the detector.

Figure 9:
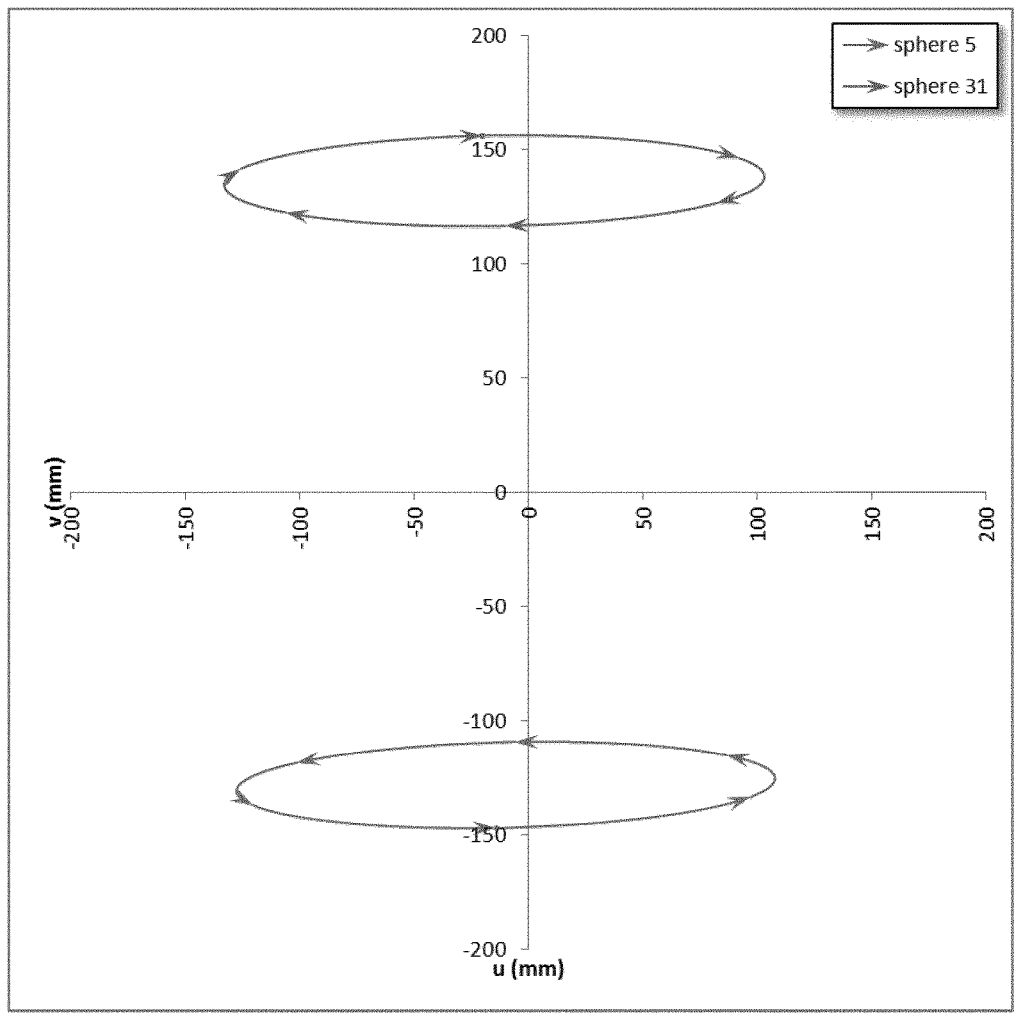
FIG. 9 is a representation of the trajectories of the image of two markers in a central scan.

FIG. 9 shows the complete trajectories of two specific markers 18 in the central scan.

Figure 10:
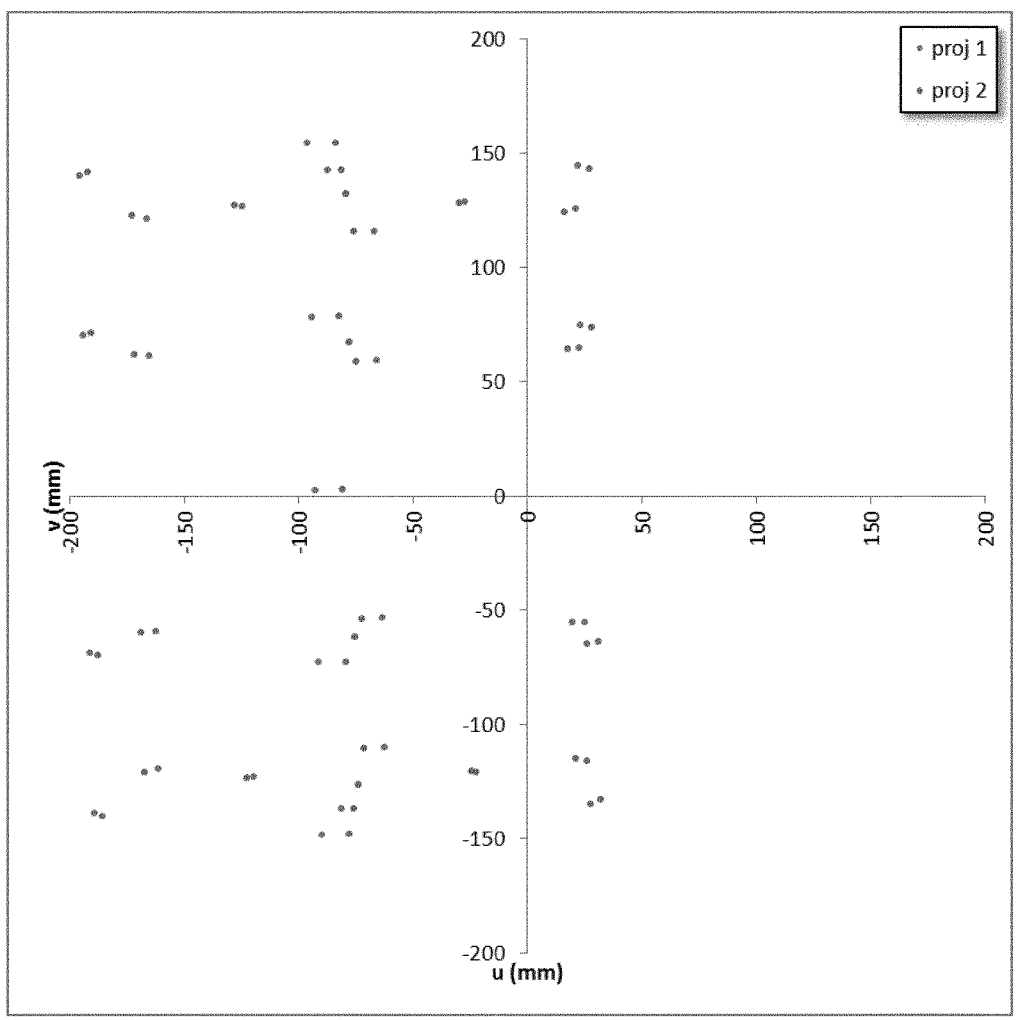
FIG. 10 shows a combination of two radiographic images of a phantom in an offset scan.

FIG. 10 shows examples of two radiographic images (projections) in the offset scan.

Figure 11:
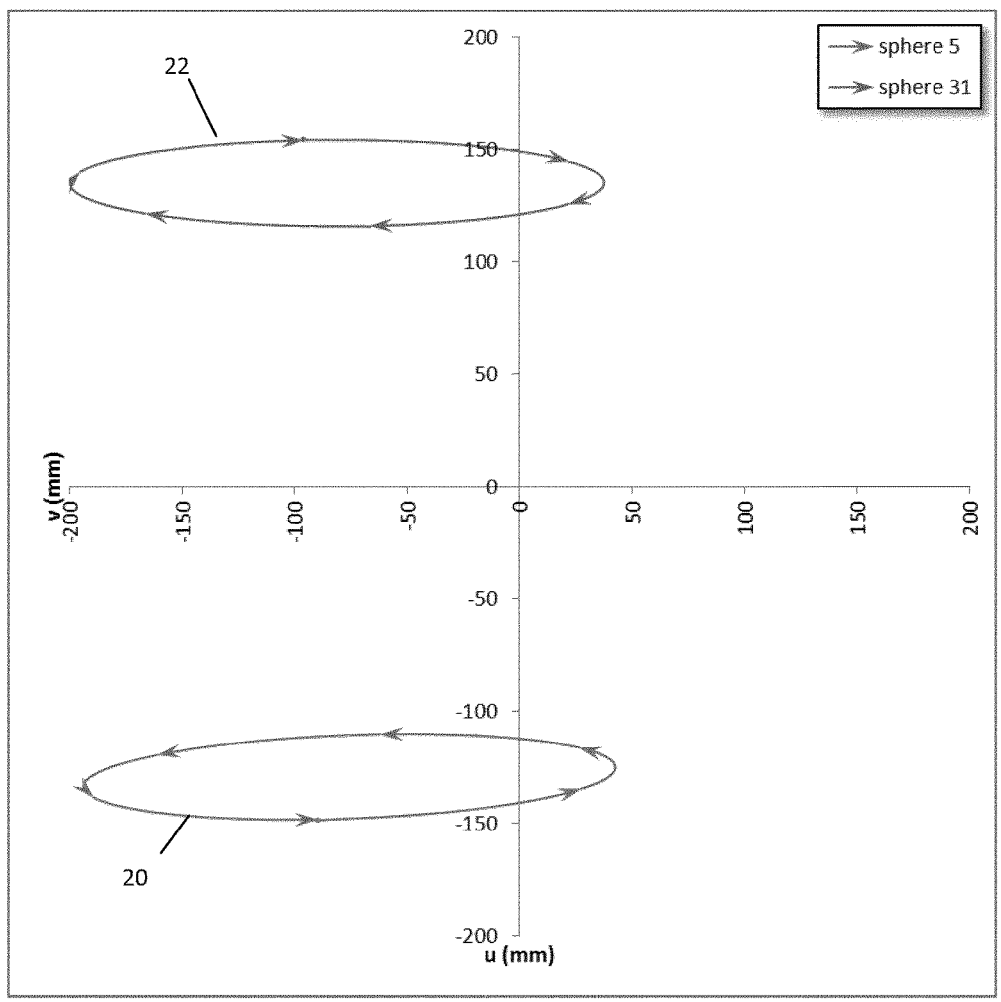
FIG. 11 is a representation of the trajectories of the image of two markers in an offset scan.

FIG. 11 shows the complete trajectories of two specific markers 18 in the offset scan.

After the N markers are identified in the images, as discussed above, 2 or more markers are selected for use in the initial estimate. In this embodiment, two markers 18 are selected, in particular, marker (sphere) number 5 and marker (sphere) number 31. The trajectories of the selected markers in the plurality of captured images is identified (different images corresponding to different projection directions of the X-rays, that is different relative positions of rotation of the calibration object). In FIG. 11, trajectory 20 corresponds to marker number 5, and trajectory 22 corresponds to marker number 31.

Figure 12:
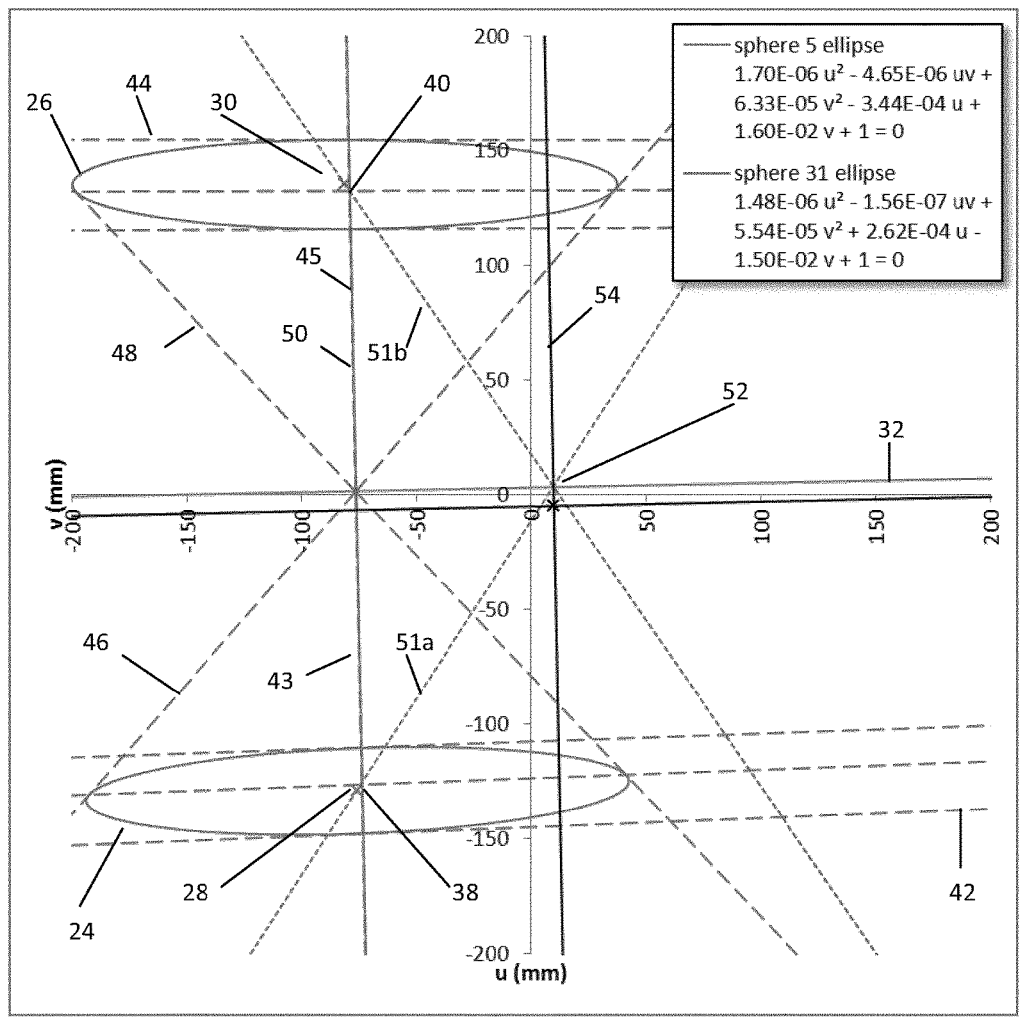
FIG. 12 is a diagram of ellipses, lines and points derived from an offset scan.
Figure 13:
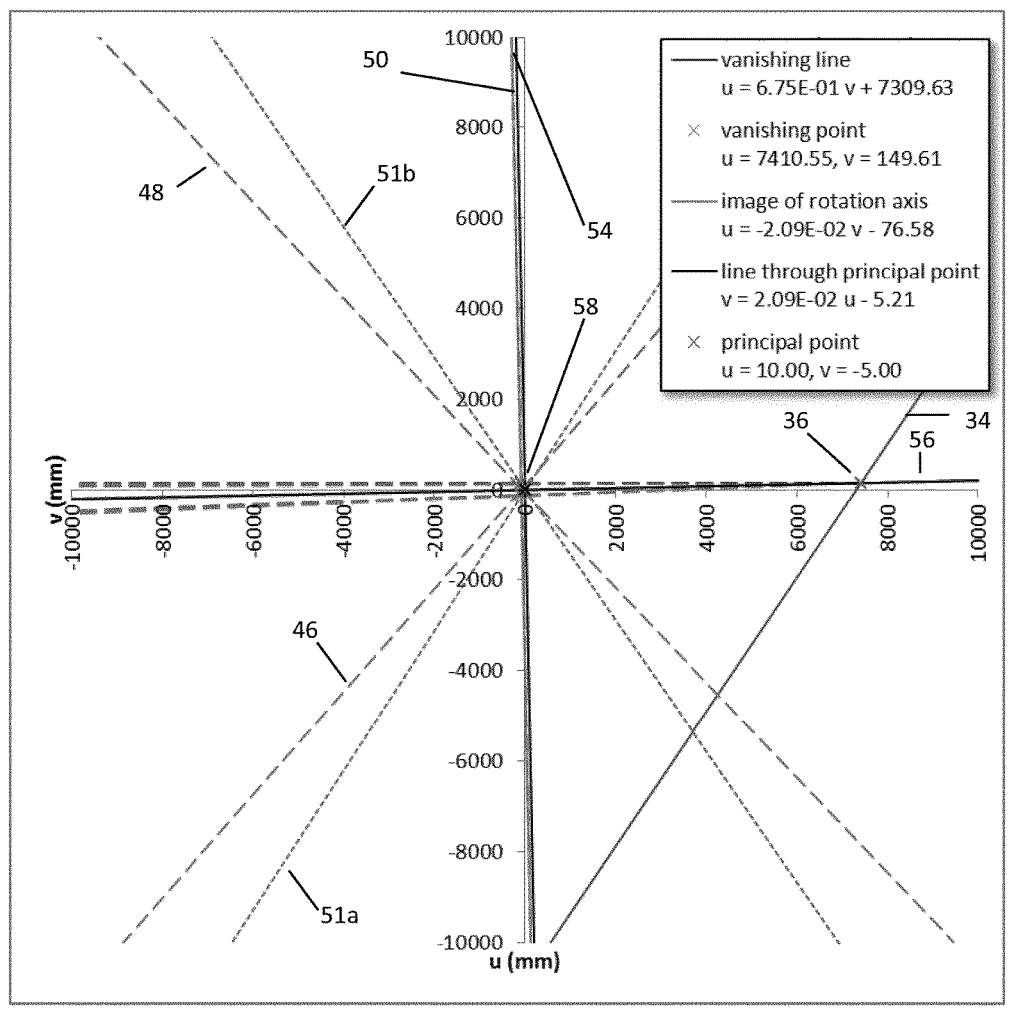
FIG. 13 is a further diagram of lines and points derived from an offset scan.

Ellipses are fitted to the trajectories of the two markers, as shown in FIG. 12. FIGS. 12 and 13 show lines and points constructed from the equations of the ellipses. The axes of FIG. 13 are on a larger scale than in FIG. 12.

Ellipses can be fitted to the two trajectories using, for example, one of the methods in [13]. Representations of the fitted ellipses, for marker 31 (top) and marker 5 (bottom) are shown in FIG. 12. In this example, the equation of the ellipse 24 of sphere 5 is (1.70E-06 $u^2$−4.65E-06 uv+6.33E-05 $v^2$−3.44E-04 u+1.60E-02 v+1=0), and the equation of the ellipse 26 of marker 31 is (1.48E-06 $u^2$−1.56E-07 uv+5.54E-05 $v^2$−2.62E-04 u−1.50E-02 v+1=0).

The centres of the ellipses can easily be determined from their equations. In the present example, the centre of the ellipse of marker 5 (indicated by a x 28 in FIGS. 12 and 13) is (u=−75.75, v=−129.35), and the centre of the ellipse of marker 31 (indicated by a x 30 in FIGS. 12 and 13) is (u=−81.28, v=134.92).

The two ellipses 24, 26 can be intersected using, for example, the methods described in [14], in particular, Chapter 11, especially section 11.4. It should be noted that the method given in [14] for solving the associated cubic equation appears to be faulty and another method such as that given in [15], in particular, page 183, can be used. The ellipses 24, 26 have no real intersections but as explained in [14] they have two pairs of complex conjugate intersections. Each complex conjugate pair can be joined to create a real line. One line 32 is the image of the central slice identified in FIG. 12. In this example, this line has equation (v=1.98E-02 u+2.69). The other line is the vanishing line 34 identified in FIG. 13. In this example, this line has equation (u=6.75E-01 v+7309.63). The intersection of the two lines is the vanishing point 36 identified in FIG. 13. In this example, the vanishing point is (u=7410.55, v=149.61).

From the equation of the image of the central slice 32 and the equations of the ellipses 24, 26 it is possible using, for example, the methods described in [10] to obtain the images of the corresponding circle centres 38, 40. Note that these are not the same as the centres of the ellipses. This can be seen in FIG. 12. The dashed lines 42, 43, 44, 45, 46, 48 in FIGS. 12 and 13 are tangents and perpendiculars to their associated ellipses in two orthogonal directions. The vanishing point 36 for one of these directions is the same one that is identified in FIG. 13. The vanishing point for the other direction is the point where the image of the rotation axis 50 intersects the image of the central slice 32. The equation of the image of the rotation axis 50 itself can be obtained by joining the images of the two circle centres and is identified in FIG. 12. In this example, this line 50 has equation (u=−2.09E-02 v−76.58).

FIG. 12 shows the line through the ellipse centre 28, 30 and corresponding image of the circle centre 38, 40, for each of the markers 5 and 31. These lines, and all similar lines for other markers, intersect the image of the central slice at a single point 52. It can be shown that the principal point 58 is located on a line which passes through this point 52 and which is perpendicular to the image of the central slice. This line 54 is identified in FIG. 12, and has the equation u=−1.98E-02 v+9.90.

It can also be shown that the principal point 58 is at the same time located on a line 56 which passes through the vanishing point 36 and which is perpendicular to the image of the rotation axis 50. This line 56 is identified in FIG. 13. The intersection of this line 56 with the previously identified line 54 gives the complete location of the principal point 58. In the present example, the line 56 through principal point 58 has equation v=2.09E-02 u−5.21, and the principal point 58 is at u=10.00, v=−5.00.

Furthermore it is noted in [16] that the perpendicular distance from the x-ray source 2 to the detector 4 (i.e. the focal length) is equal to the square root of the product of two distances along this line 56. The first distance is from the principal point 58 to the image of the rotation axis 50 and the second is from the principal point 58 to the vanishing point 36. The combination of the principal point and the focal length forms a complete description of the geometry parameters of the CT system.

The orientation of the rotation axis can be determined by calculating the vector product of two vectors in the plane of the central slice (as mentioned above, the central slice is the image of the plane that is perpendicular to the rotation axis and contains the X-ray source point, and the perpendicular to the plane is found by a vector product of vectors in the plane). One vector can be (in the plane of the detector) along the direction of the image of the central slice. The other vector can be from the x-ray source point to any point (in the plane of the detector) on the image of the central slice.

The position of the rotation axis can then be determined by selecting any point on the image of the rotation axis.

Figure 14:
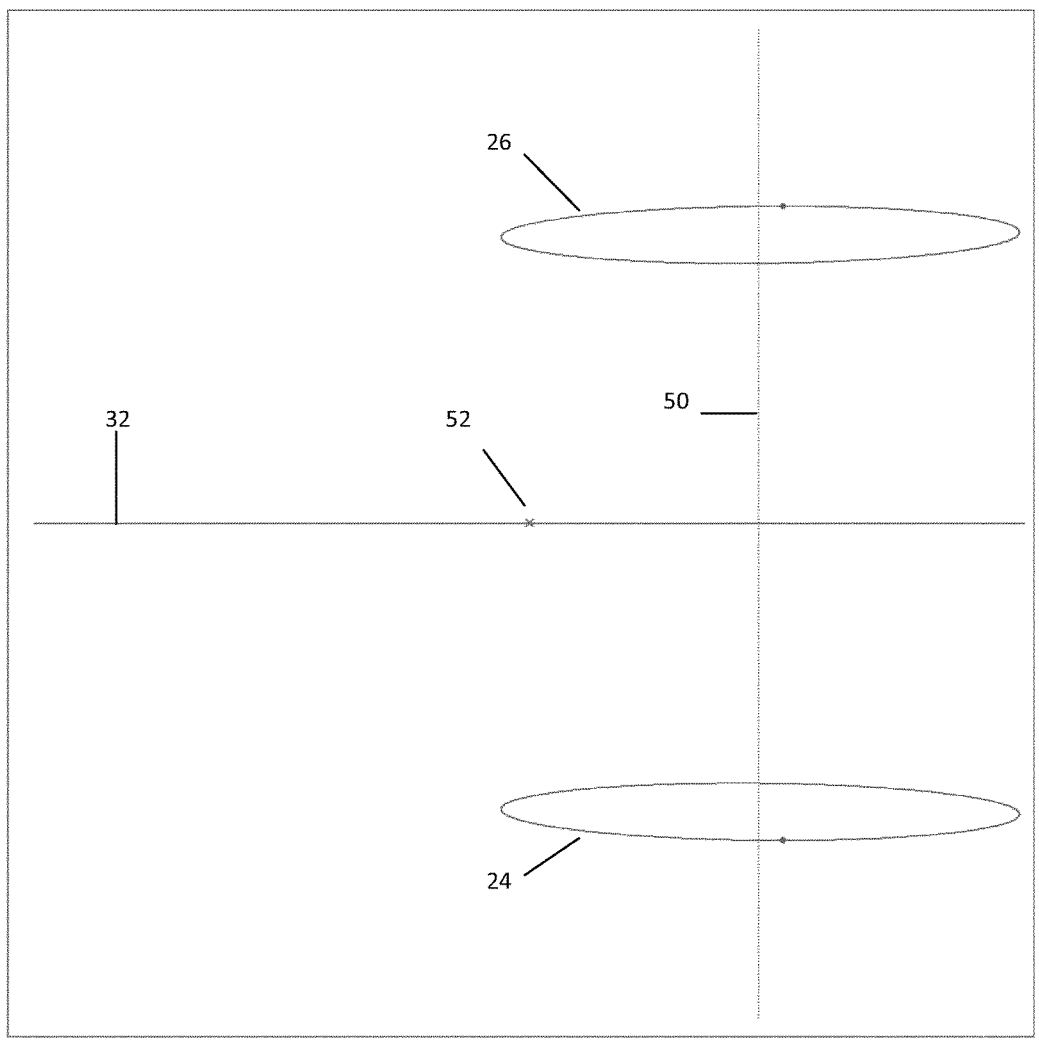
FIG. 14 illustrates geometrical parameters of the CT system.

Another example of the elliptical paths 24, 26 of two markers along with the principal point 52, the image of the central slice 32 and the image of the rotation axis 50 are shown in FIG. 14.

As described above, together this captures a complete description of the geometry parameters of the CT system and the position and orientation of the rotation axis with the exception that it is not possible to determine the perpendicular distance from the X-ray source to the rotation axis (i.e. magnification) without accurate prior information about the 3D relative positions of the markers (and specifically about the overall size of the phantom). If this distance is temporarily assigned a nominal value then an alternative value can later be substituted and the appropriate changes to the position of the rotation axis and the 3D relative positions of the markers can be trivially computed.

At this stage the inaccuracy in the 2D image coordinates of the markers stems mostly from interpolation errors but it should also be noted that the outline of a sphere is only a circle in the case that the image of the sphere is centred on the principal point. In all other cases the image of the sphere undergoes a perspective distortion and its outline becomes elliptical. Under many circumstances this effect is negligible but it can be significant when the image of the sphere is large (e.g. at higher magnifications) and is far from the principal point. Since the coordinates of the principal point and the perpendicular distance from the X-ray source point to the detector are now known (to a first approximation) it becomes possible to compensate for the perspective distortion (step 606). The points of maximum gradient (stored earlier) are transformed onto an appropriate virtual detector where they form a circle (rather than an ellipse). A new circle is fitted on this virtual detector and the diameter and centre are again stored.

Figure 15:
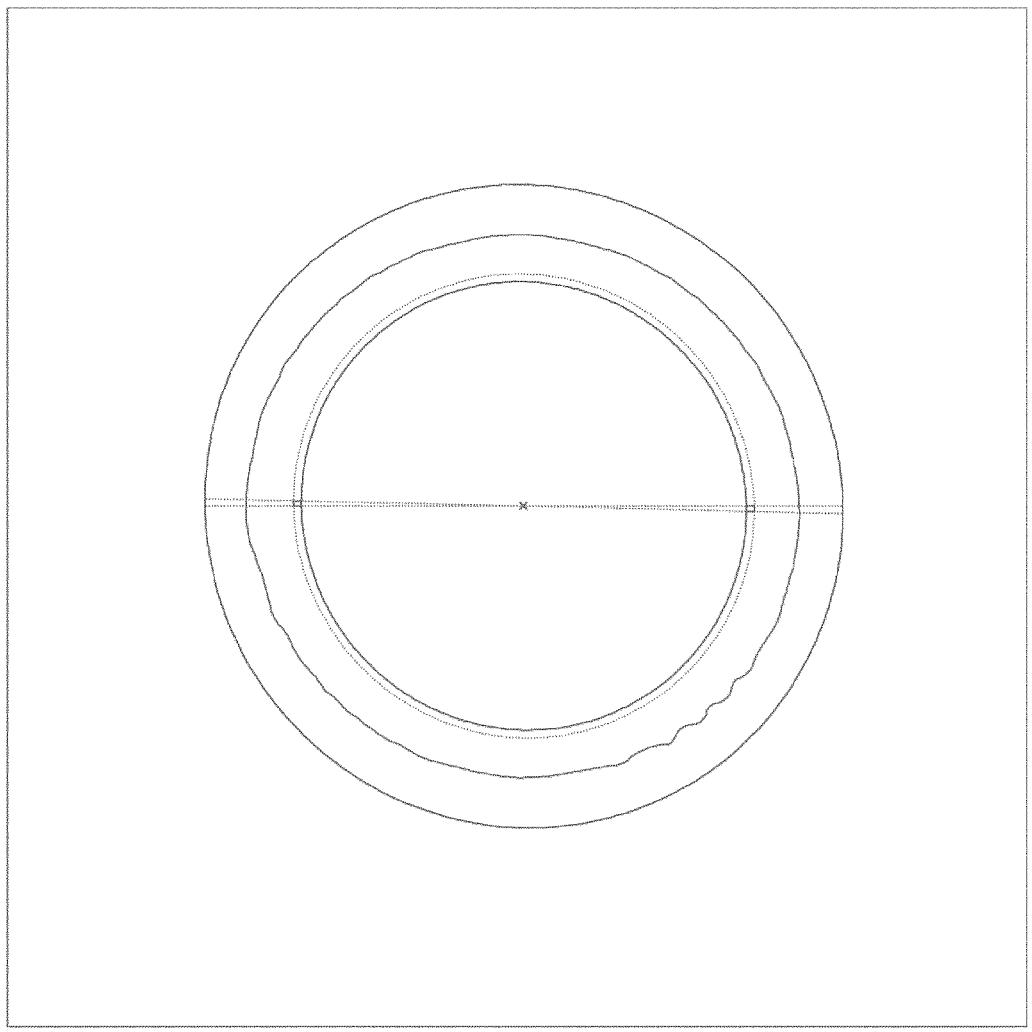
FIG. 15 illustrates a method of refining the image coordinates of markers.

The 2D image coordinates of the markers are further refined (step 607) using a slower but more accurate algorithm. This algorithm considers a narrow circular band on the virtual detector several pixels wide and containing the outline of the sphere (see FIG. 15). The algorithm seeks to maximize the area integral (over the entire circular band) of the product of the intensity at a point and the intensity at that point mirrored through the centre. A maximum will occur when the minor point is the centre of the circle. This is analogous to the maximum cross correlation method commonly used in image registration. Appropriate sampling points are constructed on the virtual detector and then transformed onto the real detector where (for example) quadratic b-spline interpolation is then used to obtain the intensity. Maximization can be via (for example) the Nelder-Mead simplex method or using gradient-based methods. Other methods can be used.

Optionally the 2D image coordinates from the slow scan are compensated to match those from the fast scan. The magnitude of the necessary compensation can be used to assess the thermal (or other) stability of the CT system and phantom, and variations such as resulting from mechanical forces such as wobble, irregularity of ball bearings, etc.

To make efficient use of all of the available data a least-squares solution using 2D image coordinates from all of the markers (and from both offset and central scans) is sought. An iterative non-linear solver is used to minimize the differences between the measured 2D image coordinates and those predicted by a model (step 608). The complete model incorporates the 3D relative positions of the markers, the geometry parameters of the CT system and the positions and orientations of the phantom (for each radiographic image). A succession of fits is performed with gradually increasing numbers of free parameters.

Using the 2D image coordinates from the offset scan and the (previously obtained) initial estimate of the geometry parameters of the CT system and of the position and orientation of the rotation axis a linear least-squares solution for the 3D relative positions of the markers is found (using a non-iterative solver). An iterative non-linear solver is then used to solve (for the offset scan only) for the complete model subject to the constraint that the phantom undergoes pure rotation (with known angular steps).

An initial estimate of the position and orientation of the rotation axis for the central scan is obtained. This can be based on (approximate) prior information about the difference in position of the central and offset scans and/or observed differences in the 2D image coordinates of one or more markers. An iterative non-linear solver is then used to refine this estimate (without attempting to solve for any other part of the model).

An iterative non-linear solver is then used to solve (simultaneously for both offset and central scans) for the complete model subject to the constraint that the phantom undergoes two separate pure rotations (with known angular steps).

An optional further step is to relax the constraint of pure rotation. Individual positions and orientations of the phantom are allowed for each radiographic image. An iterative non-linear solver is again used to find the least-squares solution which then contains a measure of the run-out and wobble of the rotation axis.

Another optional further step (step 609) attempts to detect (and quantify) a simple form of image distortion in the radiographic imaging device. The distortion is assumed to be radial with a known centre (commonly the principal point) and of the form $r'=r+a \times r^2$ where a is the value to be found and is a measure of the magnitude and direction of the distortion. The 2D image coordinates are corrected for some trial value of a and all of the initial estimates and subsequent non-linear least-squares solutions are recalculated. The final sum of square differences between the measured 2D image coordinates and those predicted by the model is a measure of the correctness of the trial value of a and a minimum can be sought. In other words, steps 604 to 608 are performed repeatedly with different magnitudes of distortion compensation, with the best result selected. Other models for image distortion can be used, such as non-radial or third-order equation models.

As previously noted, the method described so far is unable to determine the perpendicular distance from the X-ray source to the rotation axis. Correspondingly it is unable to determine the overall size of the phantom. This is a serious limitation where the CT system is a metrology CT system and accurate absolute distance measurements are required. This requires the introduction of a length standard (step 610). The method described is readily adapted to incorporate either of two possible types of length standard described below.

The first type of length standard is an accurately known distance between markers in the phantom. This can be a distance between a single pair of markers or it might be an average of two or more such distances. Given the least-squares solution based on the nominal value of the perpendicular distance from the X-ray source to the rotation axis it is trivial to compute an exactly equivalent solution where the distance between markers in the phantom in the model is equal to the known distance.

The second type of length standard is an accurately known distance between positions of the phantom. For example the acquisition can include a complete rotation of the phantom (with the rotation axis imaged in the centre of the detector) where the perpendicular distance from the X-ray source to the rotation axis is reduced by a known distance. An additional fit is required to determine the position and orientation of the rotation axis for this higher magnification scan. Again, given one least-squares solution it is trivial to compute an exactly equivalent solution where the distance between positions of the phantom in the model is equal to the known distance. It might be possible to use a bigger angular increment for this scan. The acquisition can even include several such scans where all of the incremental distances between scanning positions are known.

The above distances for the length standard can be determined using known techniques.

Further details regarding the above processing techniques are described in [7], [8], [9], [10] and [11], in the context of cameras.

The invention can be executed using a suitably programmed computer, for example, a microprocessor having software modules adapted to perform each function, or using dedicated hardware modules to perform each function, or a combination of software and hardware.

The calibration can be carried out within the CT system itself, or the data can be downloaded and transferred to another system for processing. The calibration data is then used in association with the CT system in subsequent processing, that is, when in use for imaging other objects.

Aspects and features of the invention are set out below.

An aspect of the invention provides a method of calibrating a radiographic system comprising a source and a detector, the method comprising providing a calibration object, rotating the calibration object, relative to the source and/or detector, around an axis of rotation, acquiring a plurality of radiographic images of the calibration object, assigning a nominal value representing the distance between the source and the axis of rotation, and determining geometrical parameters of the system using said radiographic images and said nominal distance value.

Another aspect of the invention provides a method of calibrating a radiographic system comprising a source and a detector, the method comprising providing a calibration object, rotating the calibration object relative to the source and/or detector, acquiring a plurality of radiographic images of the calibration object, and determining geometrical parameters of the system using said radiographic images, without measurement information regarding the calibration object (such as prior measurement, that is, prior to the determination of the parameters). In other words, the method uses an uncalibrated calibration object, that is, wherein inherent measurements of the object are not known, used or needed in the determination of the parameters of the system, by measurement before or after scanning. In the case of a calibration object comprising markers, such as in the embodiments, an uncalibrated calibration object is where the exact positions of the markers are not known.

In other words, the method is able to calibrate the system, that is, determine geometrical parameters of the system, without requiring information about the calibration object. In particular, measurements of the calibration object, obtained by measuring the calibration object, either directly such as by using a CMM, or indirectly, such as by using a system that is already calibrated, are not required to determine the geometrical parameters. This means there are greater options in the type of calibration object, because it does not need to be designed so it can be measured by a CMM, or provides greater flexibility because a specific type of calibration object is not required, prior measurement is not required, and specific measurement apparatus, such as a CMM or other calibrated system, is not required.

As described above, according to the invention, a measurement is required to determine the perpendicular distance from the X-ray source to the rotation axis, or a length standard. In other words, all the geometrical parameters of the system can be obtained without requiring measurements of the calibration object, apart from this distance measurement, which may not always be necessary in a calibration system.

Preferably, the calibration object comprises a plurality of markers, the method comprising identifying the location of the markers in the radiographic images.

Preferably, the method comprises deriving an elliptical path for each of a plurality of markers using a plurality of radiographic images, preferably by fitting an ellipse to the imaged trajectory of each of the markers.

Another aspect of the invention provides a method of calibrating a radiographic system comprising a source and a detector, the method comprising providing an object equipped with at least one marker, rotating the object relative to the source and/or detector, acquiring a plurality of radiographic images of the object, the method comprising identifying a position of an image of the at least one marker in a plurality of images, deriving a path for the at least one marker using said images, and using said path to determine geometrical parameters of the system.

According to another aspect, the invention provides a method of calibrating a radiographic system comprising a source and a detector, the method comprising providing a calibration object, rotating the calibration object relative to the source and/or detector, acquiring a plurality of radiographic images of the calibration object, wherein the calibration object comprises a plurality of markers, the method comprising identifying a plurality of markers in a plurality of images, deriving an elliptical path for each of a plurality of markers using said images, preferably by fitting an ellipse to the imaged trajectory of each of the markers, and using said elliptical paths to determine geometrical parameters of the system.

Preferably, the method comprises using the equations of the ellipses, and/or a method based on or comprising intersecting the ellipses, to determine geometrical parameters of the system.

Preferably, the method comprises deriving an initial geometry estimate of the system using said markers in said radiographic images.

Preferably, the method comprises using a circle-detection method to identify a plurality of circular shapes in each image, and selecting N or fewer of said circular shapes, where N is the number of markers in the calibration object.

Preferably, said geometrical parameters comprise one or more of the image of the rotation axis, the image of the central slice and the principal point.

Preferably, the method further comprises deriving one or more of the distance from the source to detector, object offset, rotation axis.

Preferably, the method comprises compensating for perspective distortion, for example, by projecting images of markers onto a virtual detector in which the images are more circular.

Preferably, the method comprises refining the co-ordinates of the images of the markers (circles) using a maximum cross correlation method.

Preferably, the method comprises deriving an estimated model of said calibration object, and refining said initial geometry estimate and said estimated model of said calibration object, for example, using an iterative non-linear technique.

Preferably, the method comprises analysing and compensating for residual errors, such as image distortion.

Preferably, the method comprises determining a value representing the distance between the source and the axis of rotation.

Preferably, the distance value is determined using measurements of the calibration object, or measurements of relative positions of the calibration object.

Preferably, the method comprises providing the calibration object in a central position where the axis of rotation of the calibration object approximately intersects with the beam centreline, wherein a plurality of said radiographic images are obtained with the calibration object in said central position.

Preferably, the method comprises providing the calibration object in an offset position where the axis of rotation of the calibration object is offset from the beam centreline, wherein a plurality of said radiographic images are obtained with the calibration object in said offset position.

Another aspect of the invention provides a calibration object for calibrating a radiographic system comprising a plurality of strongly X-ray attenuating spherical markers arranged within a weakly X-ray attenuating supporting material, whereby high contrast and high accuracy images of the markers can be obtained.

Preferably, the supporting material is low-density foam, such as carbon or silicon carbide foam, or plastic foam, such as extruded polystyrene foam, or solid plastics or ceramics.

Preferably, the markers are ball bearings made of tungsten carbide, steel or gold.

Preferably, the arrangement of the markers is asymmetric and/or such that they do not overlap in radiographic images.

Preferably, the markers are not fixed by adhesives.

Another aspect of the invention provides a method as set out above or below, using a calibration object as set out above.

Preferably, the method comprises performing scans at different speeds, for example, to compensate for changes in environmental conditions, such as temperature.

Preferably, the method comprises assigning a nominal value representing the distance between the source and the axis of rotation, and determining geometrical parameters of the system using said radiographic images and said nominal distance value.

Preferably, the method further comprises deriving a value for said nominal distance value, for example, using measurements of the calibration object (such as described above).

Another aspect of the invention provides a method of measuring an object in a radiographic system calibrated using a method as set out above.

Another aspect of the invention provides use of a calibration object to calibrate a radiographic system without a complete representation of the calibration object obtained by measurement means other than said radiographic system.

Another aspect of the invention provides apparatus comprising means for executing a method as set out above.

Another aspect of the invention provides a computer program or computer-readable storage medium comprising computer-executable instructions for executing a method as set out above.

REFERENCES (INCORPORATED HEREIN BY REFERENCE)

[1] EP1760457A2
[2] DE102010050949A1
[3] US20050094771A1
[4] U.S. Pat. No. 5,442,674A
[5] U.S. Pat. No. 7,147,373B2
[6] "Estimation of CT cone-beam geometry using a novel method insensitive to phantom fabrication inaccuracy: Implications for isocenter localization accuracy", J. Chetley Ford, Dandan Zheng, and Jeffrey F. Williamson, Med. Phys. 38, 2829-2840 (2011).
[7] "Camera Calibration from the Quasi-affine Invariance of Two Parallel Circles", Yihong Wu, Haijiang Zhu, Zhanyi Hu, Fuchao Wu, ECCV 2004, LNCS 3021, pp. 190-202 (2004)
[8] "Euclidean Structure from N≥2 Parallel Circles: Theory and Algorithms", Pierre Gurdjos, Peter Sturm, and Yihong Wu, ECCV 2006, Part I, LNCS 3951, pp. 238-252 (2006)
[9] "Recovering the Geometry of Single Axis Motions by Conic Fitting", Guang Jiang, Hung-tat Tsui, Long Quan, and Shang-qian Liu, CVPR 2001, ISBN 0-7695-1272-0/01 (2001)
[10] "Single Axis Geometry by Fitting Conics", Guang Jiang, Hung-tat Tsui, Long Quan, Andrew Zisserman, ECCV 2002, LNCS 2350, pp. 537-550 (2002)
[11] "Epipolar Geometry from Profiles under Circular Motion", Paulo R. S. Mendonca, Kwan-Yee K. Wong, Roberto Cipolla (2001)
[12] DE102008044437A1
[13] "A note on the least squares fitting of ellipses", Paul L. Rosin (1992)
[14] "Perspectives on Projective Geometry", Jurgen Richter-Gebert (2011)
[15] "Numerical Recipes in C", William H. Press et al. (1992)
[16] "Camera Calibration from Surfaces of Revolution", Kwan-Yee K. Wong et al. (2002)
[17] JP 4537090 B2

The invention claimed is:

1. A method of calibrating a radiographic system comprising a source and a detector, the method comprising:
providing a calibration object comprising a plurality of markers,
rotating the calibration object relative to the source and/or detector,
acquiring a plurality of radiographic images of the calibration object,
identifying the plurality of markers in the plurality of images,
deriving an elliptical path for each of the plurality of markers using said plurality of images by
assigning a nominal value representing a distance between the source and an axis of rotation of each said marker, and
determining complete geometrical parameters of the system apart from said nominal distance value using the radiographic images and said nominal distance value,
where said complete geometrical parameters are seven parameters including two parameters specifying a principal point, one parameter specifying a focal length, two parameters specifying the orientation of the axis of rotation and two parameters specifying the position of the axis of rotation, and using said elliptical paths to determine geometrical parameters of the system.

2. The method of claim 1 wherein the method does not require measurement of the calibration object.

3. The method of claim 1, the method further comprising identifying the location of the markers in the radiographic images.

4. The method of claim 3 wherein said deriving of the elliptical path fits an ellipse to the imaged trajectory of each of the markers.

5. The method of claim 1 comprising intersecting the ellipses to determine geometrical parameters of the system.

6. The method of claim 1 comprising deriving an initial geometry estimate of the system using said markers in said radiographic images.

7. The method of claim 6 comprising deriving an estimated model of said calibration object, and refining said initial geometry estimate and said estimated model of said calibration object.

8. The method of claim 7 wherein said refining said initial geometry estimate and said estimated model of said calibration object uses an iterative non-linear technique.

9. The method of claim 1 comprising using a circle-detection method to identify a plurality of circular shapes in each image, and selecting N or fewer of said circular shapes, where N is the number of markers in the calibration object.

10. The method of claim 9 further comprising deriving one or more of the distance from the source to detector, object offset, and rotation axis.

11. The method of claim 1 wherein said geometrical parameters comprise one or more of the image of the rotation axis, the image of a central slice and the principal point.

12. The method of claim 1 comprising compensating for perspective distortion, by projecting images of markers onto a virtual detector in which the projected images are more circular.

13. The method of claim 1 comprising refining the co-ordinates of the images of the markers (circles) using a maximum cross correlation method.

14. The method of claim 1 comprising analysing and compensating for residual errors, including image distortion.

15. The method of claim 14, wherein the distance value is determined using measurements of the calibration object, or measurements of relative positions of the calibration object.

16. The method of claim 1 comprising determining a value representing the distance between the source and the axis of rotation.

17. The method of claim 1 comprising providing the calibration object in a central position where the axis of rotation of the calibration object approximately intersects with the beam centreline, wherein a plurality of said radiographic images are obtained with the calibration object in said central position.

18. The method of claim 1 comprising providing the calibration object in an offset position where the axis of rotation of the calibration object is offset from the beam centreline, wherein a plurality of said radiographic images are obtained with the calibration object in said offset position.

19. The method of claim 1 using the calibration object for calibrating a radiographic system comprising a plurality of strongly X-ray attenuating spherical markers arranged within a weakly X-ray attenuating supporting material, whereby high contrast and high accuracy images of the markers can be obtained.

20. The method of claim 1 comprising performing scans at different speeds to compensate for changes in environmental conditions.

21. The method of claim 1 comprising assigning a nominal value representing the distance between the source and the axis of rotation, and detei mining geometrical parameters of the system using said radiographic images and said nominal distance value.

22. The method of claim 21 further comprising deriving a value for said nominal distance value using measurements of the calibration object.

23. The method of claim 1 comprising using an uncalibrated calibration object.

24. A method of measuring an object in a radiographic system calibrated using the method of claim 1.

25. A non-transitory computer-readable storage medium having computer-executable instructions for executing the method of claim 1 stored therein.

26. The method of claim 1 wherein said deriving of the elliptical path fits an ellipse to the imaged trajectory of each of the markers.

27. A method of calibrating a radiographic system comprising a source and a detector, the method comprising:
  providing an object equipped with a marker,
  rotating the object relative to the source and/or detector,
  acquiring a plurality of radiographic images of the object,
  identifying a position of an image of the marker in each of a plurality of images, deriving a path for the marker using said plurality of images by
    assigning a nominal value representing a distance between the source and an axis of rotation of said marker, and
    determining complete geometrical parameters of the system apart from said nominal distance value using the radiographic images and said nominal distance value,
  where said complete geometrical parameters are seven parameters including two parameters specifying a principal point, one parameter specifying a focal length, two parameters specifying the orientation of the axis of rotation and two parameters specifying the position of the axis of rotation, and
  using said path to determine geometrical parameters of the system.

28. A radiographic system having a source and a detector, the radiographic system configured to:
  rotate a calibration object comprising a plurality of markers relative to the source and/or detector,
  acquire a plurality of radiographic images of the calibration object,
  identify the plurality of markers in the plurality of images,
  derive an elliptical path for each of the plurality of markers using said plurality of images by
    assigning a nominal value representing a distance between the source and an axis of rotation of each said marker, and
    determining complete geometrical parameters of the system apart from said nominal distance value using the radiographic images and said nominal distance value,
  where said complete geometrical parameters are seven parameters including two parameters specifying a principal point, one parameter specifying a focal length, two parameters specifying the orientation of the axis of rotation and two parameters specifying the position of the axis of rotation, and
  use said elliptical paths to determine geometrical parameters of the system.

* * * * *